(12) United States Patent
Redelmeier et al.

(10) Patent No.: US 7,029,695 B2
(45) Date of Patent: Apr. 18, 2006

(54) THERAPEUTIC COMPOSITIONS CONTAINING GLUTATHIONE ANALOGS

(75) Inventors: Thomas Redelmeier, Vancouver (CA); Lawrence M. Kauvar, San Francisco, CA (US); Robert T. Lum, Palo Alto, CA (US); Matthew H. Lyttle, Point Reyes Station, CA (US); Robert W. Macsata, Pleasanton, CA (US); Steven R. Schow, Redwood Shores, CA (US); Hugo O. Villar, La Jolla, CA (US); Michael R. Kozlowski, Poway, CA (US)

(73) Assignee: Telik, Inc., Palo Alto, CA (US)

(*) Notice: Subject to any disclaimer, the term of this patent is extended or adjusted under 35 U.S.C. 154(b) by 397 days.

(21) Appl. No.: 09/903,442

(22) Filed: Jul. 10, 2001

(65) Prior Publication Data

US 2003/0100511 A1    May 29, 2003

(51) Int. Cl.
*A61K 9/127*    (2006.01)
*A61K 38/06*    (2006.01)
*C07K 5/08*    (2006.01)

(52) U.S. Cl. .......................... 424/450; 514/18; 530/331
(58) Field of Classification Search ................ 424/450; 514/18; 530/331
See application file for complete search history.

(56) References Cited

U.S. PATENT DOCUMENTS

| | | | | |
|---|---|---|---|---|
| 4,944,948 | A | * | 7/1990 | Uster et al. .................. 424/450 |
| 5,023,087 | A | * | 6/1991 | Yau-Young .................. 424/450 |
| 5,043,166 | A | * | 8/1991 | Barenholz et al. ........... 424/450 |
| 5,415,869 | A | * | 5/1995 | Straubinger et al. ......... 424/450 |
| 5,605,703 | A | * | 2/1997 | Lambiez et al. ............. 424/450 |
| 5,679,643 | A | * | 10/1997 | Kauvar et al. ................. 514/18 |
| 5,955,432 | A | * | 9/1999 | Kauvar et al. ................. 514/18 |

FOREIGN PATENT DOCUMENTS

| | | |
|---|---|---|
| EP | 1 072 608 A1 | 1/2001 |
| WO | 95/08563 | 3/1995 |
| WO | 96/40205 | 12/1996 |
| WO | WO 00/44366 | 8/2000 |

OTHER PUBLICATIONS

Ciaccio P. J. et al, "Modulation of Detoxification Gene Expression in Human Colon HT29 Cells by Glutathione-S-Transferase Inhibitors", Molecular Pharmacology, vol. 48, No. 4, Oct. 1, 1995, pp. 639-647.

Morgan A. S. et al., "Isozyme-Specific Glutathione S-Transferase Inhibitors Potentiate Drug Sensitivity in Cultured Human Tumor Cell Lines", Cancer Chemotherapy and Pharmacology, vol. 37, No. 4, 1996, pp. 363-370.

Schultz, M. et al., "Inhibitors Of Glutathione S-Transferase As Therapeutic Agents", Advanced Drug Delivery Reviews, vol. 26, No. 2/03, Jul. 1, 1997, pp. 91-104.

Z. Pavelic et al., "Development in vitro evaluation of a liposomal vaginal delivery system for acyclovir", Poster Abstract; Apr. 1, 2003; obtained from http://www.dekker.com/servlet/product/DOI/101081LPR120017490/section/abstract_38.

R.J.H. Stenekes et al., "Degradable dextran microspheres for the controlled release of liposomes", *Int. J. Pharmaceutics*, 214, 17-20 (2001).

D. Reimer et al., "Cyclosporin (CSA) release from microemulsion: effect of membrane apposition", CSPS 5$^{th}$ Symposium on Pharmaceutical Sciences '02, *J. Pharm. Pharmaceut. Sci.* (www.ualberta.ca/~csps), 5(2), 39-122 (2002).

* cited by examiner

*Primary Examiner*—Gollamudi S. Kishore
(74) *Attorney, Agent, or Firm*—Foley & Lardner LLP

(57) ABSTRACT

Pharmaceutical compositions and methods of using them. Lipid formulations of a glutathione analog and methods of manufacturing them. Their use to stimulate hematopoiesis, protect hematopoietic cells from damage caused by radiation or chemotherapy, or potentiate the stimulatory action of one or a combination of cytokines on colony formation by hematopoietic progenitor cells, protect a subject from a destructive effect of a chemotherapeutic agent or irradiation, or to potentiate the effect of a chemotherapeutic agent.

18 Claims, No Drawings

THERAPEUTIC COMPOSITIONS CONTAINING GLUTATHIONE ANALOGS

TECHNICAL FIELD

The invention relates to compositions, formulations and methods of certain glutathione analogs which interact with at least one glutathione S-transferase. The invention further relates to lipid formulations of a glutathione analog and to their process of manufacture. The lipid formulations overcome the insolubility problem of the drug when administered parenterally and decrease its toxic effects. Finally, the invention is directed to modulation of hematopoiesis in bone marrow or blood and to other useful responses provided by such compositions and formulations.

BACKGROUND AND DISCLOSURE OF THE INVENTION

The side effects of chemotherapeutic agents used in the treatment of malignancy and other indications are well known. Among these side effects are alterations in the levels of various blood cells, including neutrophils, platelets and lymphocytes. The results of these effects can be neutropenia, thrombocytopenia and general immune suppression. These side effects are not only unpleasant, but they also restrict the efficacy of cancer therapy and place the subject at serious risk of infection and uncontrolled bleeding.

At the present time, there is little practical remediation for these effects. Typically, the approaches are supportive care, large doses of antibiotics or the administration of growth factors. The administration of growth factors, such as granulocyte colony-stimulating factor (GCSF), granulocyte macrophage colony-stimulating factor (GMCSF), and more newly developed factors such as megakaryocyte growth and development factor (MGDF) and thrombopoietin (TPO) are costly. In addition, they have their own associated negative side effects.

The problems related to current approaches for managing the side effects of chemotherapy and otherwise dealing with suppression of hematopoiesis are solved, at least in part, by the biological activity of certain simple tripeptide compounds which are inhibitors of the various isoenzymes of glutathione S-transferase.

As with many small peptide-based compounds, the formulation of such compounds plays a substantial role in their solubility and efficacy. It is known that lipid formulations (*Liposomes as Drug Carriers*, ed. G. Gregoriadis, John Wiley and Sons, 1988) and emulsions or lipid microspheres (Cummings, J. et. al. Expert Opin. Ther. Pat. (1998), 8(2), 153; Takenaga, M. Adv. Drug Delivery Rev. (1996), 20(2,3), 209; Yamaguchi, T. Adv. Drug Delivery rev. (1996), 20(2,3), 117; Mizushima, Y. EP 0432697A2; Kraft, M. WO 98/05301) can be used as suitable pharmaceutical carriers that enhance solubility, modulate pharmacokinetic behavior, modify biodistribution, and protect compounds from enzymatic degradation. Increasing the lipophilicity of the compound oftentimes aids in the formulatability of compounds in emulsions and liposomes. Esters containing longer carbon chains or other lipophilic groups can, thus, be used to tailor compounds to maximize solubility.

A liposome is a completely closed lipid bilayer membrane which defines a closed aqueous compartment. Liposomes are microscopic delivery vesicles made, in part, from phospholipids which form closed, fluid-filled spheres when mixed with water. Liposomes may be either unilamellar, comprised of one lipid bilayer membrane, or multilamellar, comprised of more than bilayer. Liposomes have the potential of providing controlled release of the administered drug over an extended period of time and of reducing toxic side effects of the drug by limiting the free concentration of the active agent in the bloodstream. Liposomes can also alter the tissue distribution and uptake of drugs, and the altered tissue distribution can significantly increase the therapeutic effectiveness of the drug.

PCT application W095/08563, published Mar. 30, 1995, and PCT/US94/10797 disclose the tripeptide compounds which are analogs of glutathione. They are generally inhibitors of glutathione S-transferase activity, and the various compounds contained in this group show diverse specificities with respect to glutathione S-transferase isoenzymes. Disclosed in these patents are symmetrical esters of 1 to 10C units, with the preferred embodiment as the diethyl ester.

SUMMARY OF THE INVENTION

The invention provides pharmaceutical compositions containing compounds, and the compounds themselves, which are useful in modulating hematopoiesis generally and as aids to the chemotherapeutic treatment of tumors. The invention provides lipid formulations and methods to produce such formulations. In one aspect, the invention is directed to a method to modulate hematopoiesis from progenitor cells which comprises contacting bone marrow or peripheral blood, or fractions of these containing progenitors, with a diester of a compound of the formula A below:

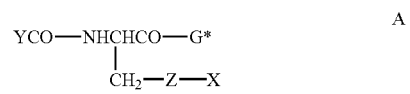

wherein:
  each ester is 1–25C;
  YCO is γ-glu or β-asp;
  G* is phenylglycine;
  Z is $CH_2$, O or S; and
  X is a hydrocarbon radical selected from the group consisting of 6–8C alkyl, benzyl, and naphthyl; or a pharmaceutically acceptable salt thereof.

In another aspect, the invention is directed to a method to modulate hematopoiesis from progenitor cells which comprises contacting bone marrow or peripheral blood, or fractions of these containing progenitors, with a diester of a compound of the formula I in a lipid formulation.

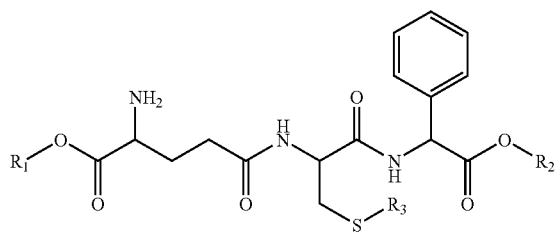

Formula I wherein:
  R1 and R2 are independently chosen from linear or branched alkyl groups (1–25C), cycloalkyl groups (6–25C), substituted alkyl groups (2–25C), heterocycles (6–20C), ethers or polyethers (3–25C) or where R1–R2 (2–20C) together form a macrocycle with formula I, and wherein R3 is a hydrocarbon radical selected from the group consisting of 6–8C alkyl, benzyl, and naphthyl; or a pharmaceutically acceptable salt thereof.

Prior to the present invention, efforts were made to increase the bioavailability of the compounds described above by producing higher alkyl esters, where at least one of R1 or R2 is a higher alkyl (at least 6C) group. This proved to be a more difficult and expensive process, however. The inventors subsequently found that by using lipid formulations, in particular, liposome formulations, they could enhance the uptake of the compounds via appropriate targeting and, therefore, increase bioavailability without having to resort to the afore-mentioned difficult, expensive production of higher alkyl esters.

Lipid formulations or compositions in accordance with the invention include liposomes, lipid microspheres, and lipid emulsions. Lipid microspheres are spherical particles composed of a lipid core and/or matrix containing the compounds of the invention. Liposomes are phospholipid vesicles consisting of lipid layer(s) bounding an aqueous compartment containg the compounds of the invention.

The compounds of formulae A or I have been shown to have limited solubility in aqueous solutions, especially in high osmotic solutions. These compounds formulated in lipids are shown to have greater solubility when placed in biological medium. These compounds have further been shown, when formulated in lipid microspheres, to have greater resistance to proteases, and an increased half-life in the presence of blood.

In one aspect, the present invention provides a method for the preparation of a lipid medium of droplets comprising of a core of compounds of formulae A or I coated with a pharmaceutically acceptable oil. Thus, the invention provides methods for the preparation of a lipid-based formulation.

In another aspect, the invention provides a method for the preparation of a phospholipid-based liposome wherein compounds of formulae A or I are found associated with the liposome.

In another aspect, the invention is directed to a process to produce phospholipid-based liposomes containing compounds of formulae A or I.

In another aspect, the invention is directed to a method to protect against the destructive effects of a chemotherapeutic agent and irradiation therapy administered to a subject, said protection including the mode of action whereby acceleration of recovery from such effects occurs, which method comprises administering the compound of formulae A or I, formulated as described to said subject in an amount and for a time effective to exert said protective effects.

In other aspects, the invention is directed to compounds, formulations, and lipid formulations containing compounds of formulae A or I for promoting the production of neutrophils, platelets and lymphocytes, restoring damaged bone marrow, protecting bone marrow from cytotoxic therapy, and exerting a protective effect against neutropenia, thrombocytopenia, lymphocytopenia and anemia caused by chemotherapy, infection or hematological diseases and for the expansion of cell populations in the course of bone marrow transplantation. Such compounds may be those of Formulae A or I presented above, or the corresponding amide, ester/amide, salt forms or free di-acid thereof. A preferred embodiment is the inclusion of low alkyl esters in lipid formulations. The invention is further directed to the use of compounds of the invention as tumor-specific chemo- or radiosensitizers, thus potentiating the effect of treatment, and as generalized chemoprotectants. Another aspect of this invention is directed to a general immune stimulant for the treatment of anemia, infections, and the like.

Another aspect of the invention is directed to the lipid formulation containing the compounds of formulae A or I which may be produced in the following manner: (I) drug and lipid are dissolved in an alcohol/water co-solvent; (ii) the mixture is rapidly diluted into a buffer to form liposomes; (iii) the liposome preparation is extruded through one or more stacked filters to generate unilamellar vesicles of a defined size; and (iv) lyophilized.

DETAILED DESCRIPTION OF THE INVENTION

Many of the compounds of formulae A and I are useful to inhibit the activity of at least one isoenzyme subclass of the glutathione S-transferase isoenzymes. Compositions of these compounds also modulate hematopoiesis in bone marrow, even in the presence of agents which normally would destroy a large percentage of the cells needed to sustain hematopoiesis. In addition, these compositions exhibit other helpful effects on bone marrow and blood cells.

Compounds of the invention of formulae A or I may be present as the free acids, salts, monoesters, diesters, monoamides, diamides or hybrid ester/amide forms. The ester or amide forms are generally those of alkyl (1–25C); alkenyl (1–25C); and arylalkyl (1–25C)-alcohols and amines. In particular, any of the diesters may include those with a first ester group having 1C atom and the second ester group having 1C, 2C, 3C, 4C, 5C, 6C, 7C, 8C, 9C, 10C, 11C, 12C, 13C, 14C, 15C, 16C, 17C, 18C, 19C, 20C, 21C, 22C, 23C, 24C or 25C atoms. Similarly, they may include those having any of the foregoing second ester groups in combination with a first ester group of 1C, 2C, 3C, 4C, 5C, 6C, 7C, 8C, 9C, 10C, 11C, 12C, 13C, 14C, 15C, 16C, 17C, 18C, 19C, 20C, 21C, 22C, 23C, 24C or 25C atoms. Such groups may be straight chain or, for those with sufficient number of atoms, have one or more branches. Particularly, at least one of the ester groups may have any one of from 10 to 25C atoms. Typical esters useful in the invention include diolelyl, palmityl/ethyl, lauryl/ethyl, dilauryl, stearyl/ethyl and the like. Especially preferred are the palmityl/ethyl forms of the compounds of formulae A or I where R3 is benzyl. Similarly, for a monoamide or monoester, the ester or amide groups may include any of the foregoing numbers of C atoms. In the case of the diamide or hybrid ester/amide forms, each of the two amide groups or the amide and ester groups can include the same combinations of C atoms described in connection with the diesters. It will be understood that such groups, and the remainder of formulae A or I, may have one or more substituents, provided such substituents do not prevent the compound from exhibiting a positive pharmaceutical effect (such as at least any one of the effects described herein). Such substituents may include one or more (such as two or three) halogens or hydroxy.

A particular diester of formulae A or I (for example, a diester of formula I) may have a greater lipophilicity than a corresponding diethyl ester. This may be particularly beneficial when the compound is formulated in a liposomal composition containing the compound. A diester may be selected which exhibits enhanced potentiation of chlorambucil cytotoxicity on human cells in comparison with the corresponding free di-acid form of the compound, as is described in Example 1 of U.S. Pat. No. 5,955,432 incorporated by reference above, or which exhibits enhanced uptake by human cancer cells such as HT-29 (human colon adenocarcinoma) suspended in serum-free medium versus the corresponding free di-acid form of the compound (as described in Example 1 of the foregoing patent). A diester may be selected which provides enhanced differentiation of mouse or rat bone marrow in comparison with the corresponding free di-acid form of the compound (as described in Example 9 of the foregoing patent).

It is evident that the tripeptides of the invention contain one or more chiral centers. The designations set forth above are directed to the genus of diastereomers which result from the presence of these chiral centers. The preferred amino acids of the invention are of L-configuration.

The compositions of the invention have several properties which make them useful as adjuncts to chemotherapy and other indicators. In the first, they modulate hematopoiesis in bone marrow, the destruction of which is a common side effect of chemotherapeutic agents. Secondly, they usually inhibit at least one class of the GST isoenzymes, including the π subclass, which is particularly prevalent in tumor cells. Finally, the compounds of formulae A or I directly potentiate the effect of chemotherapeutic agents in the destruction of tumor cells. This combination of qualities makes the compounds of the invention useful both as hematopoiesis potentiating agents directly and to ameliorate the negative effects of chemotherapeutic protocols, as well as to enhance the toxic effect to the target cells. When formulated for use in vivo or in contact with intact cells, the compounds of formulae A or I will preferably be supplied as the esters, preferably the diesters.

Formulations for administration will employ standard methods such as those described in *Remington's Pharmaceutical Sciences*, (Mack Publishing Company, Easton, Pa.) and in *Liposome Technology, Volume III, Targeted Drug Delivery and Riological Interaction* (1984, CRC Press, Inc., Boca Raton, Fla.), as well as specialized formulations as described. Particularly useful formulations for compounds of formulae A or I are lipid compositions. Lipid compositions include lipid emulsions (such as aqueous lipid emulsions), liposomes, and lipid microspheres. Formulations in lipid compositions may contain phosphatidylcholine, phosphatidylglycerol, cholesterol, phosphatidic acid, oleic acid, cardiolipin, sulfatides, gangliosides, fatty acids, peppermint oil, olive oil, soybean oil, mineral oil, peanut oil, safflower oil, corn oil, lecithin, and the like. Other materials which may comprise the formulations in lipid compositions include dipalmitoyl phosphatidylcholine (DPPC), dipalmitoyl phosphatidylglycerol (DPPG), distearoyl phosphatidylcholine (DSPC), phosphatidylethanolamine (PE), dipalmitoyl phosphatidylethanolamine (DPPE), sugar-substituted PE, dimyristoyl phosphatidylcholine (DMPC), diolyl phosphatidylcholine (DOPC), sphingomyelin, dimyristoyl lecithin (DML), dipalmitoyl lechithin (DPL), distearoyl lechithin (DSL), dilauroyl lechithin (DLL), and dioleoyl phosphatidylcholine (DOPC).

One preferred composition is that of a compound of formula I where R1 is palmityl, R2 is ethyl, R3 is benzyl, and formulated in a mixture of soybean oil, egg-yolk lecithin, and glycerol.

In the invention, the lipid may preferably comprise from 5 to 50% (W/V) of a glyceride such as soybean oil, and phospholipid (such as egg-yolk lecithin) in an amount of from 1 to 50 parts, preferably from 5 to 30 parts, per 100 parts of glyceride. It may further comprise an assisting agent of an isotonic agent such as glycerol in an amount from 1 to 50 parts, preferably 10 to 40 parts by weight. The content of the glutathione analog in a lipid composition, such as a lipid emulsion, may suitably be adjusted depending upon the form and the purpose of the emulsion, and is usually at a level of from 0.02 to 5 mg/mL.

Another preferred composition is that of a compound of formula I where R1 and R2 are ethyl, R3 is benzyl, and formulated in a mixture of egg phosphatidylcholine (EPC) and egg phosphatidylglycerol (EPG).

The lipid formulation may comprise a 3:1 to 6:1 ratio of lipid to compound of formulae A or I. Preferably, the lipid formulation may comprise by weight, 3:1, 2:2 or 1:3 parts egg phosphatidylcholine (EPC):egg phosphatidylglycerol (EPG), 1 part compound of formulae A or I, and 7 parts sucrose. Most preferably, the lipid formulation may comprise by weight, 2 parts egg phosphatidylcholine (EPC), 2 parts egg phosphatidylglycerol (EPG), 1 part compound of formulae A or I, and 7 parts sucrose. Further, additional agents such as citrate buffer may be added to control for pH. The net charge of the lipid formulation may range from negative to neutral. Preferably, the net charge of the lipid formulation is negative. The process of preparation of the lipid/compound formulation is preferably by use of an extruder, followed by filtration to generate unilamellar vesicles of a defined size of about 50–2000 nm. More preferably, the unilamellar vesicles generated will be about 50–1000 nm in size. Most preferably, the unilamellar vesicles generated will be 400–600 nm in size. The liposomes may be lyophilized to dryness and reconstituted with a pharmaceutically acceptable diluent.

Preferably, the degree of encapsulation of drug in liposome is greater than 50%, more preferably more than 80%, and final lyophilization may increase viscosity and vesicle size (75–600 nm). Most preferably, the degree of encapsulation of drug to liposome is about 95%.

Administration and use

By "modulating hematopoiesis in bone marrow or peripheral blood" is meant altering the rate of blood cell formation as measured by the capacity to form colonies or differentiated cells. Differentiated cells include neutrophils, platelets, red blood -cells, lymphocytes, macrophage, granulocytes, granulocyte-macrophage and the like. As used in the present application, "modulating hematopoiesis in bone marrow or peripheral blood" refers to the ability of bone marrow or blood treated with the compositions of the invention to exhibit colony formation or generation of differentiated cells at a level different from that of untreated bone marrow. Similarly, fractions of bone marrow or peripheral blood which contain suitable progenitors will exhibit this effect. It should be noted that, as used herein, "peripheral blood" specifically includes cord blood.

In general, when agents are employed which typically have destructive effects on bone marrow or on hematopoiesis in blood, the compositions of the invention exert a protective effect. By "protective effect" is meant that the resultant damage to the bone marrow or blood is less when the composition is administered than when it is not.

There are a number of situations in which the protective effect of the compositions of the invention are useful. These include instances where irradiation has resulted, or may result prospectively, in negative effects, instances where a subject is immunocompromised for any reason, instances wherein a subject exhibits damage to the kidneys, and instances wherein the subject has been subjected to chemotherapy. In addition, the compositions of the invention may be used in transplantation settings to increase the number of cells in the bone marrow of a donor; typically, in this case the composition may be administered in vivo or ex vivo. In this setting also, the compositions of the invention promote the movement of progenitor cells into the peripheral blood of the donor which, thus, improves the recovery of peripheral white blood cell numbers in this donor; similarly, the compositions of the invention may improve the recovery of peripheral white blood cell numbers in the recipient. In general, the compositions will improve the expansion and promote the eventual engraftment of transplanted cells after exposure to the compositions of the invention in vivo or ex vivo. The compositions of the invention can be used directly in the recipient to hasten recovery.

The compositions of the invention can be used either in vitro or in vivo. For example, these compositions can be employed to expand or otherwise modulate hematopoietic cells in bone marrow prior to allogeneic or xenogeneic transplants. Treatment of subjects using ex vivo techniques whereby expansion of relatively undifferentiated cells from the bloodstream is effectuated may also be employed. The compositions of the invention can also be formulated for in vivo administration.

When ex vivo administration is employed, either bone marrow or peripheral blood (including cord blood) or both can be directly contacted with the invention compositions, or fractions of these materials may be treated so long as the fractions contain suitable target progenitor cells.

The compounds may be formulated for injection, for oral administration, or for alternative methods of administration such as transmucosal or transdermal administration. Injection can be intravenous, intraperitoneal, intramuscular, or by any other conventional route.

The percentage of active ingredient compound (or mixture of compounds) in the formulation may vary over a wide range, such as from about 0.5% w/w to about 95% w/w or up to 100%. The preferred percentage of active ingredient will be dependent on the nature of the formulation per se. Thus, a ※pharmaceutical composition※ of a compound of the present invention may, for example, contain only the compound or the compound and other (preferably non-toxic) components. The preferred percentage of active ingredient will be dependent on the nature of the formulation per se. In addition, the compositions of the invention may be mixed with or used in addition to other beneficial agents such as immunostimulants or growth factors.

The dosage required depends on the nature of the subject, the nature of the condition, the manner of administration, and the judgment of the attending physician or veterinarian. Suitable dosage ranges are adjusted according to these parameters. In general, typical doses per patient will be in the range of 0.1–100 mg/kg per day for 10–40 days, more preferably 1–10 mg/kg per day for 14–28 days. These ranges are merely illustrative, and the correct dosage optimization can be determined by routine methods.

If the invention compositions are administered as protective agents with regard to chemotherapeutic treatment, the timing of administration may also be relevant. The timing will, however, depend on the nature of the chemotherapeutic agent used. It is clearly within routine skill to determine appropriate timing for the specific chemotherapeutic agent employed.

Diesters are chosen which preferably have a higher number of C atoms in at least one ester group and which exhibit a lower rate of hydrolysis and a higher half-life, in animal or human plasma, for example, C16/C2 versus the corresponding C2/C2 diester). Similarly, a diester may be chosen having a higher number of C atoms in at least one ester group (such as C16/C2 diester) and which exhibits enhanced modulation of hematopoiesis of animal or human cells in comparison with the corresponding diester having a lower number of ester group C atoms (such as the C2/C2 diester).

The Examples which follow serve to illustrate this invention. Further examples are provided in above-referenced U.S. Pat. No. 5,955,432 for particular compounds, and other compounds described herein can be used in an analogous manner. The Examples are in no way intended to limit the scope of this invention, but are provided to show how to make and use the compounds of this invention. In the following Examples, all temperatures are in degrees Centigrade, and RT. indicates room temperature. Glutathione analogues may be prepared by typical synthetic organic procedures well known to the art, such as those described in U.S. Pat. No. 5,786,336. In some cases, protective groups may be introduced and finally removed. Suitable protective groups for amino, hydroxyl, carboxyl groups are described in Greene, et al. ※Protective Groups in Organic Synthesis,※Second Edition, John Wiley and Sons, New York, 1991. Activation of the carboxylic acid can be achieved by using a number of different reagents as described in Larock, ※Comprehensive Organic Transformations※, VCH Publishers, New York, 1989.

Preparation of lipid emulsions and liposomes are accomplished by techniques well known to the art. Here, the soybean oil used as a glyceride is purified soybean oil, having a high purity (purity at least 99.9% as triglyceride, diglyceride and monoglyceride). The phospholipid is purified, such as egg-yolk lecithin or soybean lecithin, which may be prepared by a separation method by means of a usual organic solvent. Generally, pre-determined amounts of soybean oil, lipid, a glutathione analogue, and other additives as mentioned above are mixed and heated to form a solution and subjected to homogenizing treatment by means of a usual homogenizer (such as a pressurized jet type homogenizer or an ultrasonic homogenizer) at a temperature of 25 to 90° to obtain a water-in-oil dispersion. Then a necessary amount of water is added, and the mixture is again homogenized by means of the above homogenizer to convert it into an oil-in-water type emulsion, whereby the emulsion of the present invention is prepared. Depending upon the convenience for the production, additives such as a stabilizer or isotonic agent may be added after formulation of the emulsion.

Liposomes may be prepared according to methods known to the art and described in *Liposome Technology, Volume III, Targeted Drug Delivery and Biological Interaction* (1984, CRC Press, Inc., Boca Raton, Fla.). Liposomes may also be produced by dissolving lipid and the compounds of formulae A or I in an alcohol/water solvent, rapidly diluting the mixture in an appropriate buffer, extruding the product through at least one filter, and subsequently lyophilizing the filtrate.

EXAMPLE 1

Preparation of Glutathione Analogues

L-Glutamic acid 1, is protected using di-t-butyldicarbonate under basic conditions. Compound 2 is then cyclized to give the oxazolidinone 3 through the reaction of paraformaldehyde, and a catalytic amount of

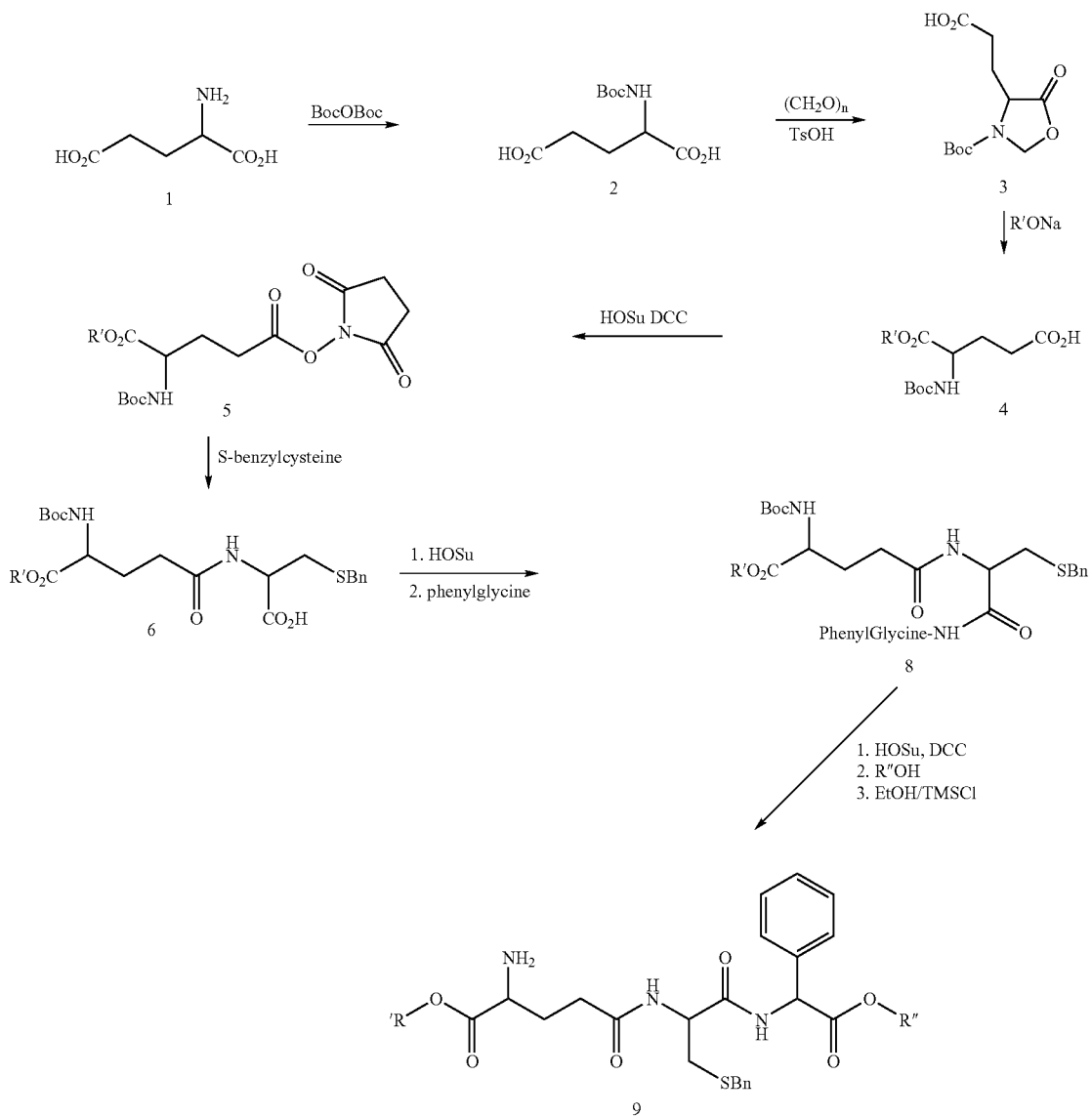

Intermediate 7 (N-a-t-Boc-a-ethyl-g-glutamyl-S(benzyl) cysteine succinimide ester) is not shown in the reaction scheme above.

p-toluenesulfonic acid. Compound 4 is prepared by the reaction of the oxazolidinone and R'ONa. The succiminide ester 5 is prepared with DCC coupling with N-hydroxysuccinimide and the g free acid 4, which is then reacted with S-benzyl-L-cysteine for the formation of the protected dipeptide 6. The succinimide ester is prepared through a DCC coupling and its reaction with phenylglycine yields the protected tripeptide, 8. Deprotection and esterification leads to final product 9.

EXAMPLE 2

N-α-t-Boc-L-glutamic Acid, 2

Two 500 g portions of L-glutamic acid (6.8 mols) were suspended in 4 L of 10% THF in water each. $Na_2CO_3$ powder was added to pH 9 resulting in a clear solution. Each solution was heated to 40° C. (for the first 10 hrs during the addition of the Boc anhydride) and 1 kg of di-t-butyl dicarbonate (4.58 mols) was added as a solid in 50 g increments to each flask every 30 min. while the pH was maintained at 9 by addition of $Na_2CO_3$. The reaction was stirred overnight at room temperature. The following day, an additional 1 kg of di-t-butyl dicarbonate was added as above. On the morning of the third day each solution was extracted twice with two 2 L each of EtOAc (It was found that the formation of the butanol stopped the reaction after the addition of 1 eq of the Boc anhydride and that the extraction with EtOAc removed it and increased the yield significantly). The aqueous layer was collected and 1 kg of di-t-butyl dicarbonate was again added as above (heating to 40° C. and adding 500 g/day in 50 g increments to each flask over a period of two days). The total reaction time was four days with the addition of 4 kg (18.32 mols) of the di-t-butyl dicarbonate. The long reaction time and heating was found essential for acceptable yields. The reaction mixtures were then extracted twice with 2 L each of EtOAc. Each of the aqueous layers were collected, cooled to 0° C. in an ice bath and acidified dropwise with conc. HCl over 30 min (1 drop/sec) to pH 3 (The BocGlu was found to be sensitive to this acidification step. If the pH was brought too low or if the HCl was added too fast, some deprotection occurred and large amounts of glutamic acid precipitated out of solution.). Upon complete acidification an off white gel formed, which was intensified by the liberal addition of NaCl to little beyond the solution's saturation point. The resulting solution was extracted twice with 2 L each of EtOAc. The removal of the Boc-L-Glu from the aqueous layer was monitored by TLC. The EtOAc layers were combined, dried over $Na_2SO_4$, filtered, and roto-evaporated at 35° C. to a clear yellowish oil. This was dried in vacuo overnight to obtain 1097.1 g of BocGlu (4.44 mols); 65 % yield.

(S)-t-Butyloxycarbonyl-5-oxo-4-oxazolidinepropanoic acid, 3

1077 g (4.36 mols) of Boc-L-Glu, 2, was dissolved in 1 L of $CH_3CN$ with warming. This was poured into a 5 L three neck flask. To this solution 3 L of benzene, 196 g (6.54 mols) of paraformaldehyde, and 40 g (0.26 mols) of p-toluene sulfonic acid were added. Equipping the round bottom flasks with two Dean-Stark apparati, dual condensers at −10° C., and a mechanical stirrer, the reaction mixture was brought to 70° C. and refluxed for 6 hours (100 ml of water was collected from the Dean-Stark apparati indicating complete reaction). The reaction mixtures, clear reddish-brown solutions, were allowed to cool to room temperature, and were rotoevaporated to a reddish-brown oil. The oil was redissolved in 2 L of ether and was extracted three times with 1 L each of water. The aqueous layers were combined and were extracted with 2 L of ether to remove the product which was in the water. Both ether layers were combined, dried over $Na_2SO_4$, filtered, and roto-evaporated to a clear yellow oil. This was dried in vacuo to obtain 952 g (3.67 mols), 84.3% yield of impure 3.

3 was purified using an open column made from a 3 L coarse sintered glass funnel modified with a 30 cm glass extension. 2 kg of Baker Silica Gel, 40 um flash chromatography packing, was slurried with 4 L of $CH_2Cl_2$ and poured into the column. The solvent was allowed to drain until it reached the resin bed. An additional 2 L of $CH_2Cl_2$ were added and allowed to drain to the resin bed settling the silica. At this point, the compound dissolved (with gentle heating) in 750 ml of $CH_2Cl_2$ was poured into the column and the solvent allowed to drain. When the solvent level reached the resin bed an additional 1 L of $CH_2Cl_2$ was added and allowed to drain to complete the loading of the product. It was then eluted with 20 L of $CH_2Cl_2$ and collected in 400 ml fractions. Evaporation to an oil, and dried to a whitish-yellow foam under a high vacuum; 745.7 g (2.88 mols), 66.2% yield was obtained.

N-α-t-Boc-L-Glutamic acid α-ethyl Ester, 4

150 g of sodium sticks (6.5 mols) were placed into a container with 500 ml of toluene, the surface tarnish was scraped off, and thin squares were cut. A 50 g portion of the squares were weighed into a tared container with 100 ml of toluene, the toluene was poured off and the sodium was added to 3 L of punctilious ethanol at 0° C. under a stream of $N_2$. After the bubbling subsided, another 50 g portion was prepared as above and added. This was repeated until the entire 200 g was added. The solution was then stirred at room temperature under $N_2$ overnight resulting in a viscous clear solution. 745.7 g (2.88 mols) of 3 was dissolved into 3 L of punctilious EtOH (with warming) and placed into a 5 L, three necked round bottom flask equipped with a mechanical stirrer. To this solution, under a stream of $N_2$, using an equalizing dropping funnel, the NaOEt was added dropwise (1 drop/sec.). The reaction was stirred overnight to produce a yellowish-white solution with a large amount of a white precipitate. The reaction mixture was chilled to 0° C. in an ice bath and conc. HCl was added dropwise (1 drop/sec.) to pH 9 (the pH was at 13 after the reaction). 6 L of water was added to produce a clear solution. This was extracted twice with 3 L each of a 1:1 mixture of ether:petroleum ether. The aqueous was collected, chilled to 0° C. in an ice bath, and while stirring, HCl was added dropwise (1 drop/sec) to pH 3. The acidified solution was extracted twice with 3 L ether each. The ether layers were combined, dried over $Na_2SO_4$, filtered, and evaporated to a clear yellow oil. This was dried under a high-vacuum to give 609 g (2.11 mols), 73.5% yield.

N-α-t-Boc-L-Glutamic Acid α-ethyl Ester γ-succinimide Ester, 5

609 g (2.11 mols) of N-α-t-Boc-L-Glutamic acid α-ethyl ester 4, and 280.4 g of N-hydroxysuccinimide (2.43 mols) were dissolved in 3 L of $CH_2Cl_2$ in a 5 L, three neck round bottom, equipped with a mechanical stirrer. 547.1 g of N,N'-dicyclohexylcarbodiimide (2.65 mols) was dissolved in 500 ml of $CH_2Cl_2$ and was added dropwise, with stirring, under a stream of $N_2$. An additional 50 g of DCC (0.24 mol) was dissolved in 100 ml of $CH_2Cl_2$ and added dropwise to the reaction mixture and stirred overnight. TLC showed complete reaction. The DCC urea was filtered from the reaction mixture, and the filtrate was rotoevaporated to an oil and dried to a foam under a high vacuum; 1042.7 g (2.81 mols) of crude 5 was obtained.

5 was purified using the open column used for the purification of 3. 1.5 kg of Baker Silica Gel, 40 μm flash chromatography packing, was slurried in 4 L of $CH_2Cl_2$ and poured into the column. This was allowed to drain until the solvent level reached the resin bed. An additional 2 L of $CH_2Cl_2$ was added and allowed to drain to the resin bed in order to pack the silica. When the solvent level reached the top of the resin bed, the compound dissolved (with gentle heating) in 750 ml of $CH_2Cl_2$ was poured into the column and allowed to load by gravity. When the solvent reached the resin bed, 1 L of $CH_2Cl_2$ was added and allowed to drain in order to completely load the product. The product was eluted with 20 L of $CH_2Cl_2$ and collected in 400 ml aliquots. Fractions were evaporated to an oil, and dried to a foam under a high vacuum; 853 g (2.28 mols), 108.0% yield (note purity in supplement #5) was obtained.

N-α-t Boc-α-ethyl-γ-glutamyl-S(benzyl)-L-cysteine, 6

465 g (2.2 mols) of S(benzyl)-L-cysteine was slurried in 4 L of a 20% THF and water solution. $Na_2CO_3$ powder was added to the solution while stirring magnetically to pH 9. This produces a partially dissolved slurry. 853 g (2.28 mols) of 5 was dissolved in 1.5 L of THF with gentle heating. This was added dropwise (2 drop/sec) to the stirring solution while maintaining the pH at 9 with $Na_2CO_3$. The reaction mixture was extracted twice with 2 L each of 1:1 ether:petroleum ether. TLC was checked to ensure that the product remained in the aqueous phase due to the large amount of THF. The aqueous phase was separated and chilled to 0° C. in an ice bath. Concentrated hydrochloric acid was added dropwise while the solution was stirred magnetically until the pH reached 3. The oily precipitate produced was then extracted into two 2 L portions of ether. The ether layers were combined, poured over $Na_2SO_4$, filtered, evaporated to an oil, and dried to a foam under a high vacuum giving 895.8 g (1.91 mols), 90.4% yield.

N-α-t-Boc-α-ethyl-L-γ-glutamyl-L-S(benzyl)cysteine succinimide ester, 7

895 g (1.91 mols) of 6, and 240.6 g of N-hydroxysuccinimide (2.09 mols) were dissolved in 3 L of $CH_2Cl_2$ in a 5 L, three neck round bottom, equipped with a mechanical stirrer. 472.5 g of N,N'-dicyclohexylcarbodiimide (2.29 mols) was dissolved in 500 ml of $CH_2Cl_2$ and was added dropwise (2 drops/sec) with stirring, under a stream of $N_2$. After 5 hrs, a TLC showed a substantial amount of starting material. An additional 50 g (0.24 mol) of DCC was dissolved in 50 ml of $CH_2Cl_2$ and added dropwise to the reaction mixture and stirred overnight. TLC showed complete reaction. The DCC urea was filtered from the reaction mixture, and the filtrate was evaporated to 1 L. Ether was added to cloud point and the solution was chilled to 0° C. in an ice bath. Upon scratching crystals began to form. Small amounts of ether were added to maintain cloud point and push out the product. The solution was stored at 4° C. overnight. The crystals were collected by filtration and dried under a high vacuum; 953 g (1.67 mols), 87.4% yield was obtained.

N-α-t-Boc-α-ethyl-L-γ-glutamyl-L-S(benzyl)cystenyl-R-phenylglycine, 8

253 g (1.67 mols) of (R)-(−)-phenylglycine was slurried in 4 L of a 20% THF and water solution. $Na_2CO_3$ powder was added to the magnetically stirred solution to a pH of 9, producing a partially dissolved slurry. 953 g (1.67 mols) of 7 was dissolved in 1.5 L of THF with gentle heating. This was added dropwise (2 drop/sec) to the stirring solution while the pH was maintained at 9 by addition of $Na_2CO_3$. The reaction was stirred 6 hours resulting in a clear yellowish-orange solution. The reaction mixture was extracted twice with 2 L each of 1:1 ether:petroleum ether. TLC was checked to ensure that the product remained in the aqueous layer due to the large amount of THF. The aqueous layer was separated and chilled to 0° C. in an ice bath. While magnetically stirring the solution, hydrochloric acid (conc.) was added dropwise (1 drop/sec) until the pH reached 3. The product was then extracted twice with 2 L each of ether. The ether layers were combined, poured over $Na_2SO_4$, filtered, evaporated to an oil, and dried to a foam under a high vacuum yielding 853 g (1.45 mols), 86.8% yield.

γ-Glutamyl-S(benzyl)cysteinyl-R-phenyl glycine diethyl ester hydrochloride, 9

767.5 g (1.26 mols) of 8 was divided into two portions and each dissolved in 2.4 L of punctilious EtOH in 5 L three neck round bottoms equipped with mechanical stirrers. Each solution was placed into an ice bath and chilled to 0° C. while stirring under a stream of argon. 385 ml (6.32 mols) of $(CH_3)_3SiCl$ was added dropwise (1 drop/sec) to each solution while the temperature was maintained at 0° C. After the $(CH_3)_3SiCl$ was added (2.5 hrs), the reactions were taken out of their ice baths and allowed to warm to room temperature. The reactions are stirred overnight. After 18 hours, the reaction mixtures become a white solid mass. The solid is then broken up to form a slurry and each is rotoevaporated at 30° C. to a volume of 2 L each. While stirring vigorously with the mechanical stirrers, 2 L of anhydrous ether is added dropwise (1 drop/sec.) to each slurry over a period of 2.5 hours at room temperature. The insoluble material was collected by filtration. The filter cakes are dried overnight under a high vacuum to yield a combined total of 312.8 g of 9. This 312.8 g was dissolved in 7 L of hot $CH_3CN$ (79° C.) with stirring, filtered hot to remove insoluble material, and the filtrate allowed to cool to room temperature. As the solution cooled, small white needle-like crystals began to form and when it reached room temperature it solidified to a solid mass. This was broken up and the solid was collected by filtration. The filter cake was dried 16 hours under a high vacuum over NaOH pellets. The dried material was to afford 277.0 g (0.49 mol), 38.8% yield was obtained. Compounds 10, 11, and 13 are obtained in a similar manner. Compound 12 is obtained from compound 8 following removal of the t-Boc group by cleavage with concentrated HCl.

TABLE 1

Description of Substituents R1, R2, and R3 in Compounds 9–13

| Compound | R1 | R2 | R3 |
|---|---|---|---|
| 9 | $CH_2CH_3$ | $CH_2CH_3$ | Benzyl |
| 10 | $(CH_2)_7CH_3$ | $CH_2CH_3$ | Benzyl |
| 11 | $(CH_2)_{15}CH_3$ | $CH_2CH_3$ | Benzyl |
| 12 | $(CH_2)_{15}CH_3$ | H | Benzyl |
| 13 | $(CH_2)_9CH_3$ | $CH_2CH_3$ | Benzyl |

EXAMPLE 3

Preparation of Lipid Microspheres 30 mg of 9, 10 g of purified soybean oil, and 1.8 g of purified yolk lecithin were added, and the mixture was melted under heating by means of a homogenizer. Then 2.21 gm of glycerol and enough distilled water to bring the volume to 100 ml (approximately 90 mL) were added, followed by a rough emulsification by means of a homogenizer. The product is then further emulsified by means of a manton gaulin type homogenizer. The solution is then passed through a 1.2 µm filter to afford a final emulsion of approximately 220 nM particles at 300 µg/mL. In a similar manner, lipid microspheres containing compounds 10 to 12 are prepared.

TABLE 2

Measured Characteristics of Lipid Microspheres

| Compound | Conc. (mg/mL) | Particle Size Mean ± SD (nM) | Incorporation of compound in Lipid Particle Fraction of 1.2 µm-filter passing (%) | Decrease of $K_1$ in esterase hydrolysis |
|---|---|---|---|---|
| 9 | 0.1–1 | | 93.7 | 0.609 |
| 10 | 0.03–3 | 220.7 ± 106.3 | 96.8-1-5.9 | 0.454 |

TABLE 2-continued

Measured Characteristics of Lipid Microspheres

| Compound | Conc. (mg/mL) | Particle Size Mean ± SD (nM) | Incorporation of compound in Lipid Particle Fraction of 1.2 μm-filter passing (%) | Decrease of $K_I$ in esterase hydrolysis |
|---|---|---|---|---|
| 11 | 1–3 | 219.6 ± 76.0 | 90.6–91.3 | 0.185 |
| 12 | 0.3 | 222.3 ± 76.4 | 91.9 | |

The decrease of $K_I$ reported in Table 2 above is an indicator of enhanced bioavailability of the glutathione analogs of the invention. Variations and modifications to the above described invention are, of course, possible. Accordingly, the present invention is not limited to the embodiments described in detail above.

EXAMPLE 4

Liposome Manufacturing Process

Unless otherwise stated, the following general procedure is used to manufacture the lipid formulation: (i) 1573 mg compound 9, 3146 mg of egg phosphatidylcholine (EPC), and 3146 mg of egg phosphatidylglycerol (EPG), are dissolved in 14.3 ml anhydrous ethanol and 2.2 ml $H_2O$ by mixing at ambient temperature; (ii) the solution is taken up in a 30 ml syringe using a 20 gauge needle and injected directly (within 1 minute) into 80.9 ml of stirred 370 mM sucrose to form multilamellar vesicles (MLVs); (iii) 2.5 ml of 1 M citrate (pH 4.0) is added to the stirred buffer; (iv) the solution is extruded ten times through two stacked 80 nm polycarbonate filters using a 100 ml EXTRUDER (Lipex Biomembranes, Vancouver Canada) to form unilamellar vesicles; (v) passed through 0.22 micron filters to sterilize; and (vi) lyophilized to remove water and ethanol. The lyophilization cycle involved rapid freezing of the sample (2.5 ml fill of 10 ml vial) to a sample temperature of −50° C., followed by lyophilization at a tray temperature of −35° C. for 42 hours to remove primary water, and for 2 hours at 20° C. to remove secondary water.

Quasi Elastic light Scattering (QELS) on the samples was carried out to determine the average vesicle size using a Nicomp Particle Sizer (Model 270). The level of drug incorporation (% encapsulation) in the vesicles is determined using two independent approaches. In the first approach, 0.1 ml of formulation is placed on a 1.0 ml tuberculin syringe containing hydrated sephadex G-50; the sample is centrifuged for 5 min. at 2,000 rpm in a table-top Centrifuge and the vesicles are recovered (>70%) in the void volume. Unencapsulated or precipitated drug is removed by this process, and remains on the gel filtration column. The level of encapsulation (%) is calculated from the drug/lipid ratio prior to and following column chromatography. A second approach relies upon separation of the liposomes from unencapsulated drug by centrifugation through Micron30 filters with a MW cutoff of 30,000 Daltons (Amicon). The level of encapsulation (%) is calculated from 1−([Free Drug]/[Total drug])*100.

EXAMPLE 5

Formulation of 9 in Lipids Using Dilution from Ethanol

The results presented in Table 3 below summarize the incorporation of 9 in several lipid formulations as a function of drug/lipid ratio and lipid composition. Dilution of the ethanol solution into a sucrose buffer results in the spontaneous formation of liposomes (termed multilamellar vesicles, MLVs) which are relatively large (average diameter of 700 nm), heterogeneous, but do not contain visible lipid or drug precipitates. The MLVs may be passed (5–10×) through stacked polycarbonate filters (pore size of 80 nm) using an EXTRUDER (Lipex Biomembranes, Vancouver, Canada). This process removes the precipitated form of the drug (<2%), and reduces the vesicle size to an average diameter of 140 nm (+/−20 nm).

TABLE 3

Incorporation of Compound 9 into Liposomes by Ethanol Dilution

| Drug/Lipid (wt/wt) | Lipid Composition | Drug (mg/ml) | Encapsulation (Microcon, %) | Size (nm) |
|---|---|---|---|---|
| 0.25 | EPC | 16.2 | 56 | 69 (+/− 22) |
| 0.14 | EPC | 12.9 | 80 | 101 (+/− 40) |
| 0.25 | EPC/EPG (9/1) | 13.6 | 60 | 69 (+/− 19) |
| 0.14 | EPC/EPG (2.2/1) | ND | ND | ND |
| 0.14 | EPC/EPG (1/1) | 14.4 | 99 | 92 |

ND signifies not determined.

EXAMPLE 6

Effect of Lyophilization and Vesicle Size

The results presented in Table 4 below summarize the relation between lyophilization conditions and the resulting vesicle size, and level of drug encapsulation. Unless otherwise stated, vesicles were prepared as described in Example 4, sterile filtered and vialed in 2.5 ml aliquots. The vials were subsequently frozen to a sample temperature of −50° C. for sufficient time to reduce the sample temperature to the shelf temperature. The samples were then exposed to the indicated shelf temperature in the presence of a vacuum (50 to 200 mTorr) for sufficient time to remove the primary water (24 to 48 hours), and subsequently to ambient temperature for 2–6 hours.

TABLE 4

The Influence of Different Lyophilization Cycles on Compound 9 Liposomes

| Drug/Lipid (wt/wt) | Lipid Composition | Sucrose (mM) | Lyophilization Conditions | Encapsulation (Microcon, %) | Size (nm) |
|---|---|---|---|---|---|
| 0.25 | EPC | 300 | Uncontrolled | 73 | 2844 |
| 0.14 | EPC | 300 | Uncontrolled | 87 | 8871 |
| 0.14 | EPC | 700 | −10° C. | 85% | NA |
| 0.14 | EPC/EPG (1/1) | 300 | −10° C. | 99 | 1418 |
| 0.14 | EPC/EPG (1/1) | 700 | −10° C. | 98 | 535 |
| 0.14 | EPC/EPG (1/1) | 700 | −30° C. | 99 | 491 |

EXAMPLE 7

Influence of Drug/Lipid Ratio on Encapsulation Level

The results provided in Table 5 below summarize the influence of the initial drug/lipid ratio on the level of encapsulation. Compound 9 can be efficiently encapsulated in EPC/EPG liposomes at drug/lipid ratio of up to 0.33 (wt/wt).

TABLE 5

Encapsulation of Compound 9 in EPC/EPG Liposomes, as a Function of Drug/Lipid Ratio

| Drug/Lipid (wt/wt) | Lipid Composition | Sucrose (mM) | Lyophilization Conditions | Encapsulation (Microcon, %) | Size (nm) |
|---|---|---|---|---|---|
| 0.50 | EPC/EPG (1/1) | 300 | Uncontrolled | ND | ND |
| 0.33 | EPC/EPG (1/1) | 300 | Uncontrolled | 99 | 1402 |
| 0.25 | EPC/EPG (1/1) | 300 | Uncontrolled | 100 | 715 |
| 0.20 | EPC/EPG (1/1) | 300 | Uncontrolled | 100 | 750 |

EXAMPLE 8

Vesicle Size Stability

For all batches examined, the level of encapsulation was not influenced by storage at 2–8° C. for up to 48 hours as shown in Table 6 below.

TABLE 6

Stability of Vesicles Size Following Extrusion, as a Function of Ethanol Content

| Drug/Lipid (wt/wt) | Lipid Composition | Ethanol (%) | 0 hr | 2 hr | 24 hr | 48 hour |
|---|---|---|---|---|---|---|
| 0.25 | EPC/EPG (1/1) | 15 | 161 nm | 156 nm | 179 nm | 160 nm |
| 0.25 | EPC/EPG (1/1) | 20 | 120 nm | 123 nm | 273 nm | ND |

EXAMPLE 9

Effect of Lyophylization Time on Encapsulation

The results presented in Table 7 below summarize the influence of lyophilization conditions on the encapsulation efficiency, viscosity, and size of a compound 9 EPC/EPG formulation.

TABLE 7

The Influence of Primary Lyophilization Cycle on Encapsulation, Vesicle Size and Viscosity of Compound 9 EPC/EPG Formulations

| Drug/Lipid (wt/wt) | Lipid Composition | Sucrose (mM) | Lyophilization Time (hr) | Encapsulation (Microcon, %) | Size (nm) | Viscosity |
|---|---|---|---|---|---|---|
| 0.25 | EPC/EPG (1/1) | 300 | 32 | 99 | 611 | Negligible |
| 0.25 | EPC/EPG (1/1) | 300 | 40 | 99 | 391 | Negligible |
| 0.25 | EPC/EPG (1/1) | 300 | 44 | 97 | 584 | Negligible |
| 0.25 | EPC/EPG (1/1) | 300 | 54 | 98 | 502 | Viscous |
| 0.25 | EPC/EPG (1/1) | 300 | 59 | 98 | 636 | Very Viscous |

EXAMPLE 10

Rat Model of Chemotherapy Induced Neutropenia

Compound 9 formulated as described in Example 4 accelerated recovery from chemotherapy-induced neutropenia in rats. Male CD rats (250–300 g) were injected intraperitoneally with either the antineoplastic drug, fluorouracil (125 mg/kg) or an equivalent volume of its vehicle (saline). Beginning one day after the fluorouracil injection, each fluorouracil-treated rat was given 8 daily intravenous injections of either Compound 9 (35 mg/kg, n=4), G-CSF (10 μg/kg, n=5), or vehicle (saline, n=4). Rats originally injected with saline rather than fluorouracil received saline intravenously (n=7). Blood samples were taken for measurement of neutrophil levels prior to the fluorouracil and every 1 to 2 days thereafter for 14 days. The accelerated recovery from fluorouracil-induced neutropenia by lyposomally-formulated Compound 9 is shown in FIG. 1.

EXAMPLE 11

Effect of Compound 9 on Normal Rats

Compound 9 as described in Example 4 (35 mg/kg, i.v.) also increased circulating neutrophil levels in normal rats (FIG. B). Male, CD rats (250–300 g) were given 5 daily intravenous injections of either Compound 9 (35 mg/kg, n=9), G-CSF (10 μg/kg, n=4), or vehicle (saline, n=11). Blood samples were taken for measurement of neutrophil levels daily. The elevation of circulating neutrophil levels by lipid-formulated Compound 9 in the normal rat is shown in FIG. 2.

What is claimed is:

1. A liposomal formulation containing a compound that is:
   (i) a diester of a compound of formula A

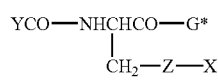

where:
each ester is 1–25C;
YCO is γ-glu or β-asp;
G* is phenylglycine;
Z is $CH_2$, O or S; and
X is a hydrocarbon radical which is alkyl (6–8C), benzyl, or naphthyl;
or a pharmaceutically acceptable salt thereof; or (ii) a compound of formula I

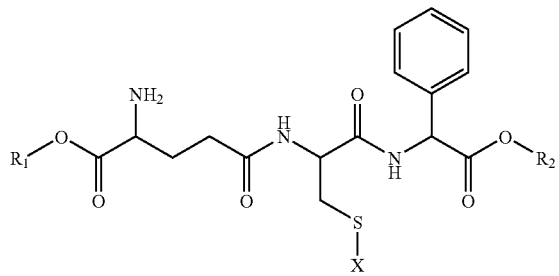

where:
$R_1$ and $R_2$ are each independently linear or branched alkyl (1–25C), cycloalkyl (6–25C), heterocycle (6–25C), ether or polyether (3–25C), or $R_1$ and $R_2$ together have 2–20C atoms and form a macrocycle with the remainder of formula I; and
X is as defined above for formula A;
or a pharmaceutically acceptable salt thereof
where the lipids of the liposomal formulation consist of egg phosphatidylcholine and egg phosphatidylglycerol in a ratio of 0.75–1.25:0.75–1.25 by weight and the ratio of lipids to compound is 3.5–4.5:0.5–1.5 by weight.

2. The liposomal formulation of claim 1 where the compound is γ-glutamyl-S(benzyl)cysteinyl-R-phenylglycine diethyl ester or a pharmaceutically acceptable salt thereof.

3. The liposomal formulation of claim 1 where the ratio of lipids to compound is 3:1–6:1 by weight.

4. The liposomal formulation of claim 1, having
   (i) at least 50% degree of encapsulation of the compound; and
   (ii) an average vesicle size of 50–2000 nm.

5. The liposomal formulation of claim 4 where the degree of encapsulation is above 80%.

6. The liposomal formulation of claim 4 where the vesicle size is 400–600 nm.

7. The liposomal formulation of claim 1 which consists essentially of 1 part compound, 2 parts egg phosphatidylcholine, 2 parts egg phosphatidylglycerol, and 7 parts sucrose by weight.

8. The liposomal formulation of claim 7 which consists essentially of 1 part γ-glutamyl-S(benzyl)cysteinyl-R-phenylglycine diethyl ester or a pharmaceutically acceptable salt thereof, 2 parts egg phosphatidylcholine, 2 parts egg phosphatidylglycerol, and 7 parts sucrose by weight.

9. The liposomal formulation of claim 8 which comprises lyophilized liposomes consisting essentially of 1 part γ-glutamyl-S(benzyl)cysteinyl-R-phenylglycine diethyl ester or a pharmaceutically acceptable salt thereof, 2 parts egg phosphatidylcholine, 2 parts egg phosphatidylglycerol, and 7 parts sucrose by weight.

10. A method of preparing a liposomal formulation containing a compound that is:
(i) a diester of a compound of formula A

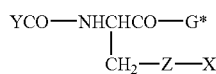

where:
each ester is 1–25C;
YCO is γ-glu or β-asp;
G* is phenylglycine;
Z is $CH_2$, O or S; and
X is a hydrocarbon radical which is alkyl (6–8C), benzyl, or naphthyl;
or a pharmaceutically acceptable salt thereof; or
(ii) a compound of formula I

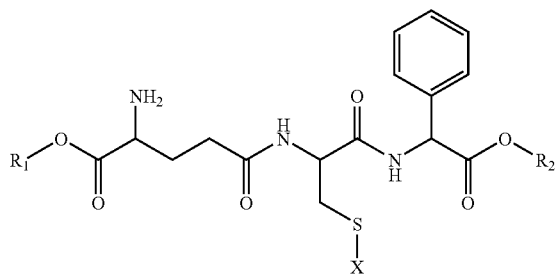

where:
$R_1$ and $R_2$ are each independently linear or branched alkyl (1–25C), cycloalkyl (6–25C), heterocycle (6–25C), ether or polyether (3–25G), or $R_1$ and $R_2$ together have 2–20 C atoms and form a macrocycle with the remainder of formula I; and X is as defined above for formula A;
or a pharmaceutically acceptable salt thereof;
which method comprises formulating the compound in a liposomal composition
where the lipids of the liposomal formulation consist of egg phosphatidylcholine and egg phosphatidylglycerol in a ratio of 0.75–1.25:0.75–1.25 by weight and the ratio of lipids to compound is 3.5–4.5:0.5–1.5 by weight.

11. The method of claim 10 where the compound is γ-glutamyl-S(benzyl)cysteinyl-R-phenylglycine diethyl ester or a pharmaceutically acceptable salt thereof.

12. The method of claim 10, further comprising extrusion.

13. The method of claim 10, further comprising lyophilization.

14. The method of claim 10 which comprises dissolving 1 part γ-glutamyl-S(benzyl)cysteinyl-R-phenylglycine diethyl ester or a pharmaceutically acceptable salt thereof, 2 parts egg phosphatidylcholine, and 2 parts egg phosphatidylglycerol in ethanol/water, injecting the solution into water containing 7 parts sucrose, and extruding to form a liposomal formulation.

15. The method of claim 14 which comprises dissolving 1 part γ-glutamyl-S(benzyl)cysteinyl-R-phenylglycine diethyl ester or a pharmaceutically acceptable salt thereof, 2 parts egg phosphatidylcholine, and 2 parts egg phosphatidylglycerol in ethanol/water, injecting the solution into water containing 7 parts sucrose, extruding to form a liposomal formulation, and lyophilizing the liposomal formulation to form lyophilized liposomes.

16. A liposomal formulation prepared by the method of claim 14.

17. A lyophilized liposomal formulation prepared by the method of claim 15.

18. A method for modulating hematopoiesis or protecting against the destructive effects of chemotherapy comprising administering to a subject in need thereof a liposomal formulation according to any one of claims 1, 2, 3, 4 to 9, 16, and 17.

* * * * *